United States Patent [19]

Gilbaugh, Jr. et al.

[11] Patent Number: 4,711,250
[45] Date of Patent: Dec. 8, 1987

[54] HAND-HELD MEDICAL SYRINGE ACTUATOR DEVICE

[76] Inventors: James H. Gilbaugh, Jr., 2902 SW. Canterbury, Portland, Oreg. 97201; Charles B. Willock, 16222 SE. Oatfield Rd., Milwaukie, Oreg. 97222

[21] Appl. No.: 905,788

[22] Filed: Sep. 9, 1986

[51] Int. Cl.$^4$ ............................................. A61M 5/00
[52] U.S. Cl. .................................. 128/765; 604/223; 604/228
[58] Field of Search ........................ 128/749, 751-755, 128/757-758, 760, 763, 765-767, 771; 604/63, 134-135, 181, 187, 218, 223, 227, 229, 236-238, 242-243

[56] References Cited

U.S. PATENT DOCUMENTS

| | | | |
|---|---|---|---|
| 2,892,457 | 6/1959 | Sturtz | 604/223 |
| 3,115,135 | 12/1963 | Sarnoff | 604/228 |
| 3,577,980 | 5/1971 | Cohen | 604/237 X |
| 3,819,091 | 6/1974 | Hollender | 604/223 X |
| 4,036,232 | 7/1977 | Genese | 128/765 X |
| 4,178,810 | 12/1979 | Takahashi | 128/751 X |
| 4,198,975 | 4/1980 | Haller | 604/223 X |
| 4,305,406 | 12/1981 | Megahed | 128/766 |
| 4,323,066 | 4/1982 | Bourdon | 604/228 |
| 4,340,051 | 7/1982 | Leibinsohn | 604/227 |
| 4,421,123 | 12/1983 | Percarpio | 128/766 |
| 4,441,509 | 4/1984 | Kotsifas et al. | 128/757 |
| 4,530,695 | 7/1985 | Phillips et al. | 604/134 X |
| 4,542,749 | 9/1985 | Caselgrandi et al. | 128/752 |
| 4,594,073 | 6/1986 | Stine | 128/765 X |
| 4,601,711 | 7/1986 | Ashbury et al. | 604/187 X |
| 4,605,011 | 8/1986 | Naslund | 128/752 |

Primary Examiner—Kyle L. Howell
Assistant Examiner—Angela D. Sykes
Attorney, Agent, or Firm—Klarquist, Sparkman, Campbell, Leigh & Whinston

[57] ABSTRACT

The invention is directed toward a hand-held syringe actuator and removable syringe. The syringe acutator includes a stationary part which removably receives a flange of the syringe barrel and a movable finger part which removably receives a flange at the end of the syringe plunger. The finger grip is movable upon application of finger pressure, but is spring biased to urge the plunger into the syringe barrel. A valve operating stem, carried by the actuator, slidably extends through the finger grip and through the plunger, extending into the syringe barrel and terminating in a valve element. The valve element is sized to seat in a valve seat provided in the syringe barrel at the closed end of the barrel. A spring urges the valve member to remain seated on the seat. The device is constructed so that it can be held and manipulated by the use of only one hand.

In one form of device, a latch is provided and can be activated to releasably hold the valve element off of its seat.

11 Claims, 12 Drawing Figures

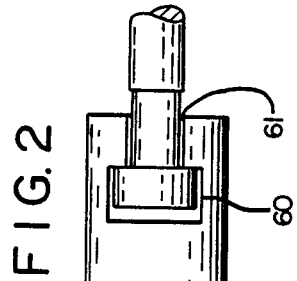
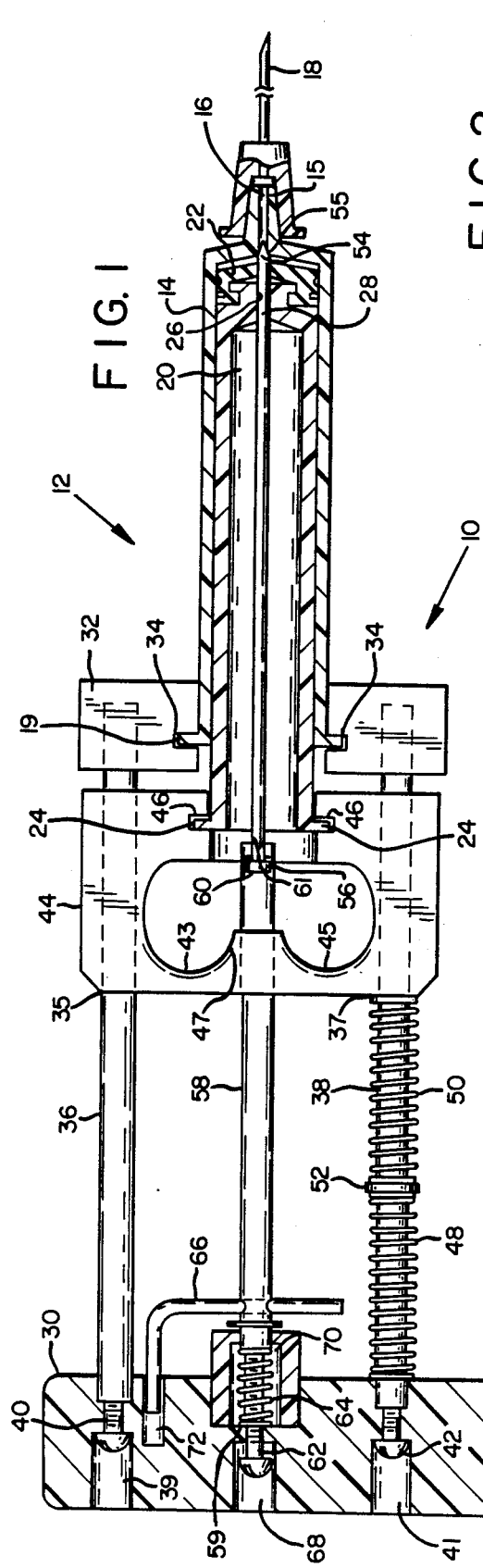
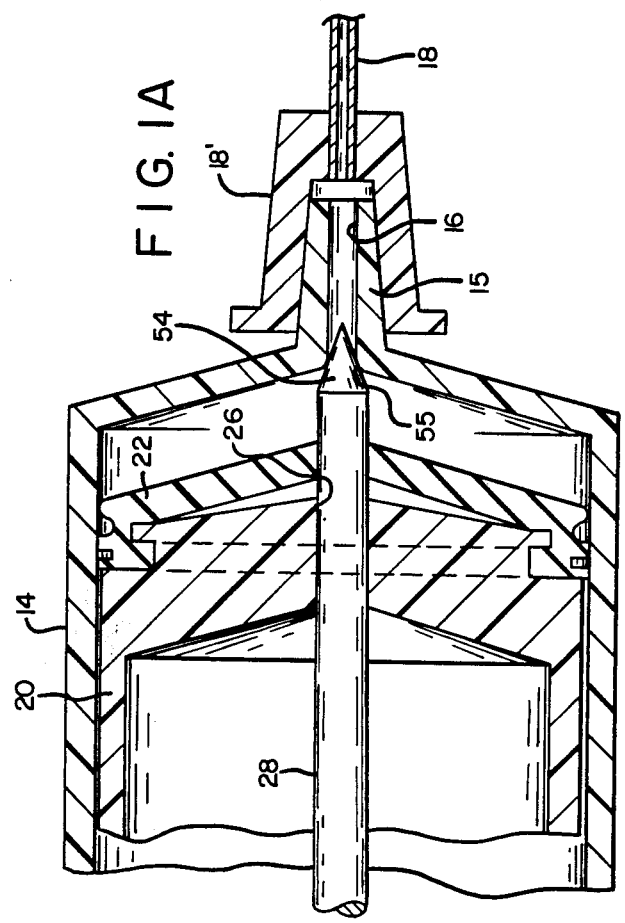

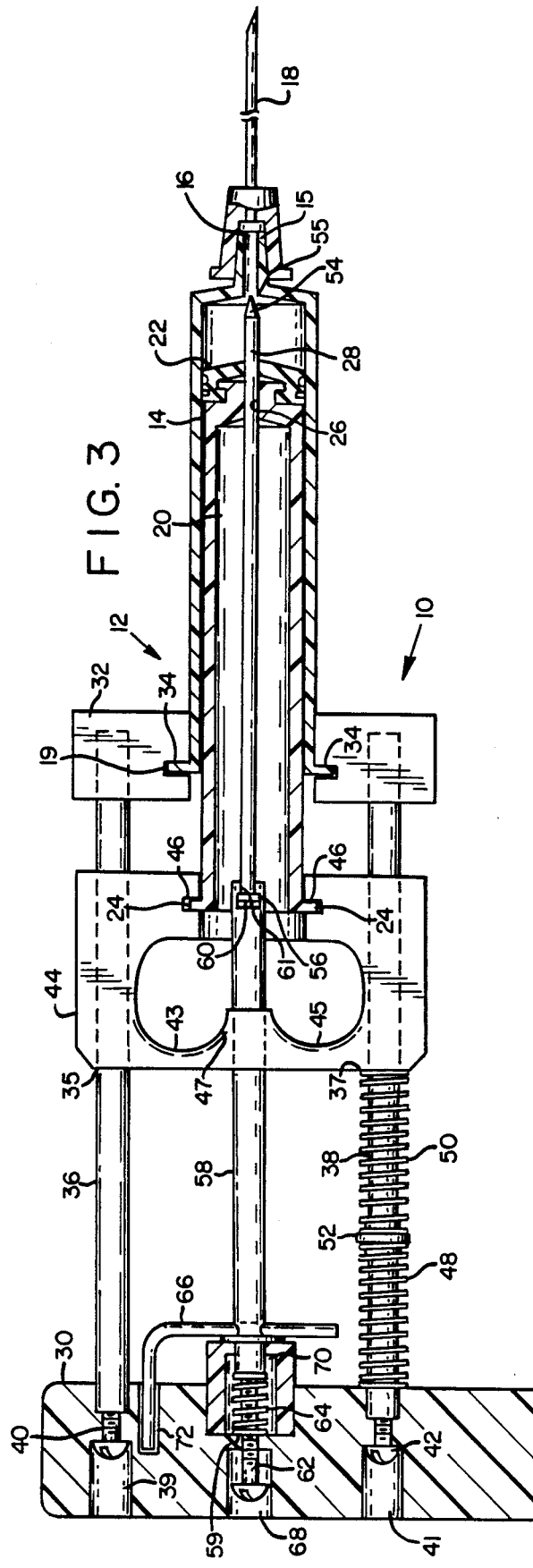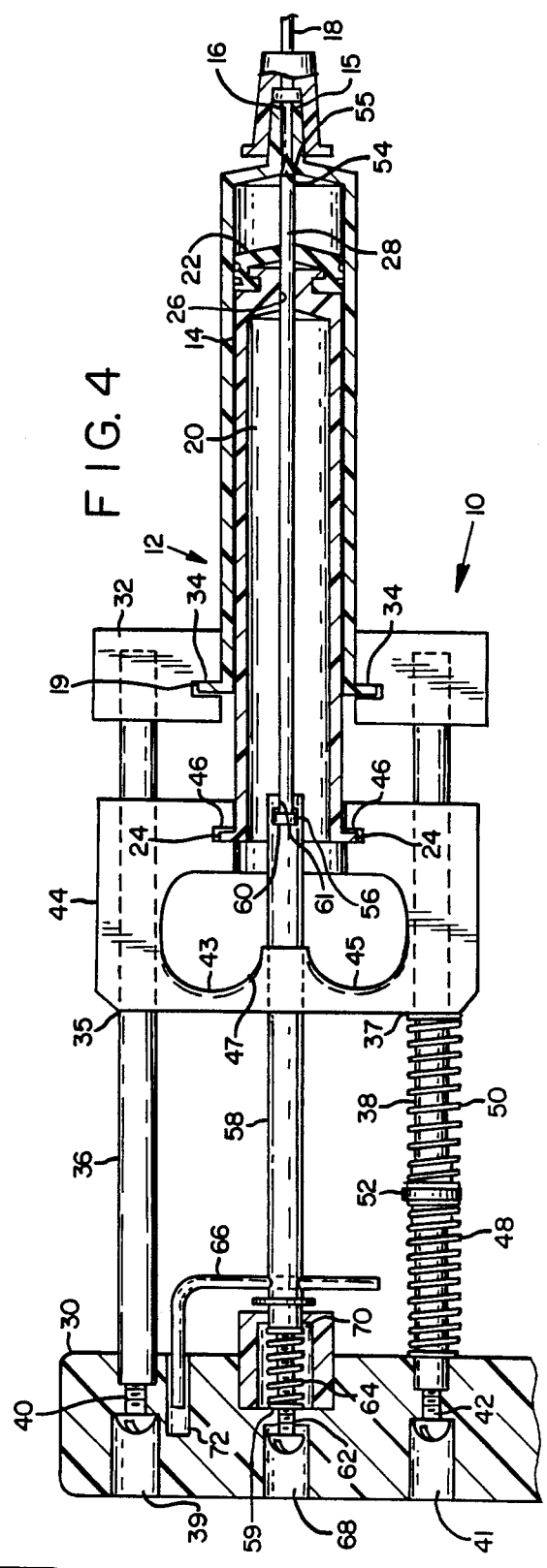

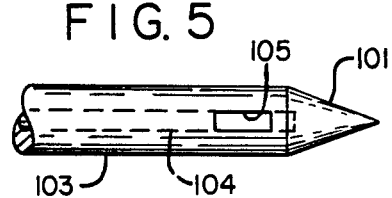
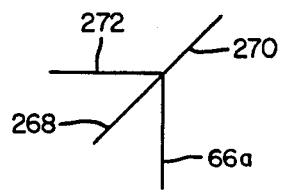
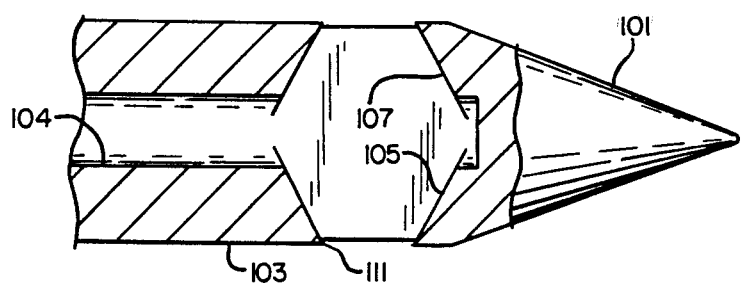
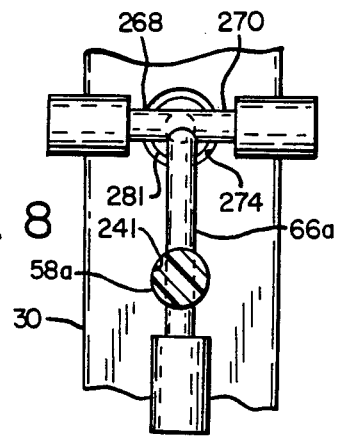
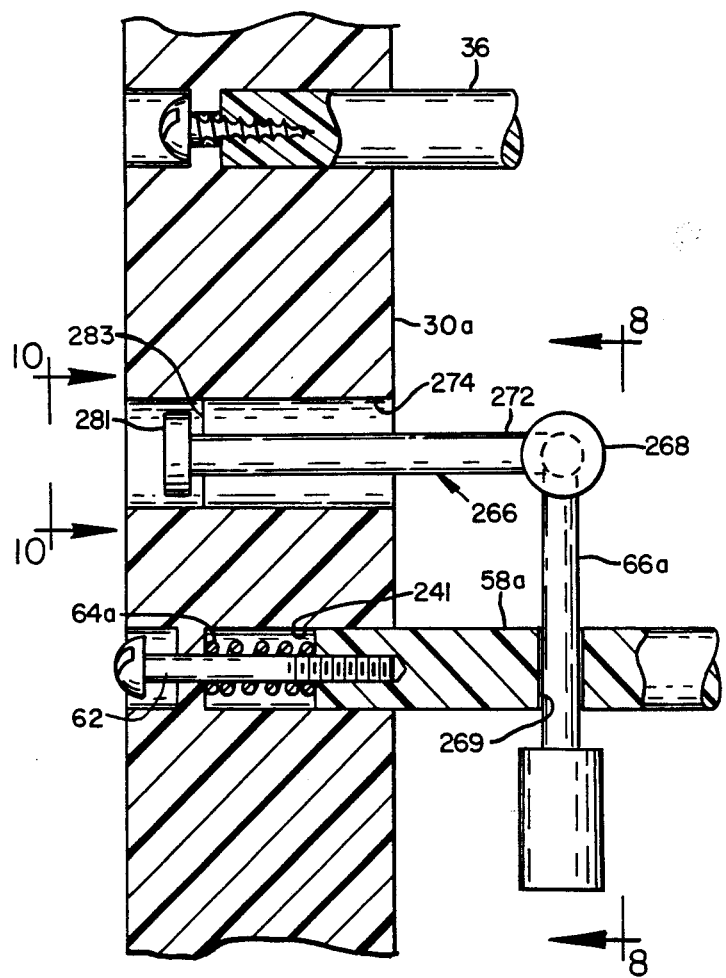
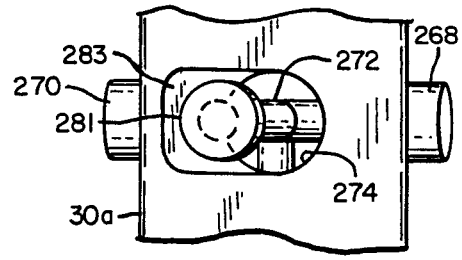
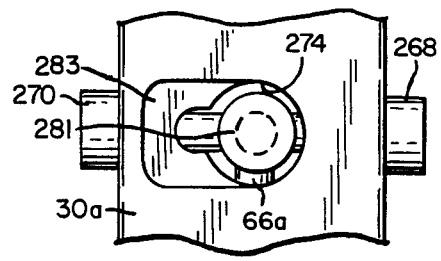

HAND-HELD MEDICAL SYRINGE ACTUATOR DEVICE

This invention relates generally to medical devices and more particularly to a medical device in the form of a hand-held syringe actuator for operating a removable syringe.

Devices of the above type broadly are old, for example, as sold by the Precision Dynamics Corporation of Burbank, Calif. as the CAMECO syringe; as sold by Orion Industries of Indianapolis, Ind. as the Control II syringe; and as described in U.S. Pat. No. 3,819,091 to Hollender. Devices of this general type can be used for a variety of purposes, such as withdrawing body fluids, injecting a fluid into a body, or both.

Other devices for injecting or aspirating fluids relative to a body are shown in U.S. Pat. Nos. 4,323,066 to Bourdon; 3,115,135 to Sarnoff; 2,892,457 to Sturtz; 4,198,975 to Haller; and 4,340,051 to Leibinsohn. For example, Bourdon discloses a syringe having two coaxial pistons interconnected by a shaft, the first piston being in direct contact with the fluid, the second piston being isolated in a larger control cylinder. The second cylinder is divided into two chambers by the second piston with an orifice extending through the piston and interconnecting the chambers. The orifice is opened or closed by the relative position of a valve member adjustable by a user by moving an interconnected shaft extending from the rear of the syringe. Positive or negative pressure in the second chamber relative to the first chamber when the orifice is blocked results in controllable movement of the first piston. Such a device has the drawbacks of being relatively complex and requiring an independent pressure source for causing the pressure differentials within the second cylinder.

The patent to Leibinsohn discloses a finger pressure cushioning device for a syringe to prevent a user from applying too much pressure when injecting fluid into a body.

The patents to Sturtz and Haller disclose pistol-like syringe hand grips.

The patent to Sarnoff discloses a hypodermic cartridge holder for receiving a replaceable associated cartridge.

The foregoing syringes have several drawbacks, including requiring the use of more than one hand when aspirating and subsequently discharging fluid or cells.

SUMMARY OF THE INVENTION

The present invention is directed toward a hand-held syringe actuator and a removable syringe, primarily intended for body fluid removal as a substitute for a biopsy. The syringe is removably fitted in the hand-held actuator so that upon actuation of the device, the plunger in the syringe barrel is withdrawn thus creating an aspirating effect to withdraw fluid from a body organ or other portion of the body for test purposes.

In use of such a device, I have discovered that it is important that the device be so constructed that it can be held and manipulated by the use of only one hand, leaving the other hand free for other purposes.

It is therefore a main object of the present invention to provide such a device.

Another feature of the invention is an improved needle so constructed that not only fluids can be withdrawn, but also enabling cells, such as cancer cells, to be withdrawn.

A device incorporating the invention comprises a hand-held pistol grip syringe actuator, a stationary part which removably receives a flange on the syringe barrel, and a movable finger grip part which removably receives a flange at the end of the plunger. The finger grip is movable upon the application of finger pressure, but is spring-biased to urge the plunger into the syringe barrel. A valve operating stem, carried by the body, slidably extends through the finger grip and through the plunger, and then extends into the syringe barrel and terminates in a valve element. The latter is sized to seat in a valve seat provided in the syringe barrel at the closed end of the barrel. A biasing means urges the valve member to remain seated on the seat.

After a needle on the barrel is inserted into an organ or other part of the body, the pistol grip is actuated by withdrawing the plunger with the finger grip. Frictional contact between the plunger and the stem, as the plunger is retracted, unseats the valve element. Fluid and cells from the body are caused to enter the needle and possibly the lower end of the syringe barrel.

The above arrangement is such that although the finger grip spring urges the finger grip back to its original discharge position, the valve member spring will act, as soon as the retracting force of the finger grip is stopped, to cause the valve to seat. Seating of the valve member causes fluid within the lower end of the plunger and needle to be trapped and accordingly holds the plunger in a withdrawn position.

The user, upon removing the needle from a body, can then turn to a slide or other sample receiving means and, by means of a valve stem tripper on the device, positively unseat the valve, whereupon the finger grip spring causes it and the plunger to move to expel the fluids from the needle.

Various other objects of the invention will be apparent from the following description taken in connection with the accompanying drawings.

BRIEF DESCRIPTION OF THE DRAWINGS

FIG. 1 is a side view, partly in section, of the medical syringe device, shown as releasably holding a syringe and plunger, the plunger being in its fully discharge or extended position.

FIG. 1A is an enlarged sectional view of the operative end portion of the syringe;

FIG. 2 is an enlarged view of the valve stem interconnection;

FIG. 3 is a sectional view of the syringe in a retracted position with the needle valve being disengaged;

FIG. 4 is a sectional view of the medical syringe in a partially retracted position with the needle valve being closed;

FIG. 5 is an enlarged view of an improved needle;

FIG. 6 is a further enlarged cross section of a portion of the needle;

FIG. 7 is a fragmentary view of the hand piece of a modified form of invention;

FIG. 8 is a fragmentary section taken along line 8—8 of FIG. 7;

FIG. 9 is a schematic view to show the relationship of the arms of an actuator of the modified form of the invention;

FIG. 10 is a fragmentary view taken in the direction of the arrows 10—10 of FIG. 7; and FIG. 11 is a view like FIG. 10 but showing the latched condition of the actuator.

DETAILED DESCRIPTION OF A PREFERRED EMBODIMENT

Referring to the drawings, the syringe-type medical device comprises a holder 10 for holding a specially modified syringe 12. The syringe is adapted to be replaceable with respect to the holder.

Apart from modifications of the present invention, syringe 12 is generally conventional in construction having a cylinder or barrel 14 which narrows to a nipple 15 (FIG. 1A) having a discharge orifice 16. The nipple detachably retains a needle 18 at its end for insertion into a body. The needle has an adapter piece 18' for frictionally fitting on the nipple 15. The end of the cylinder opposite the discharge orifice terminates in a laterally extending and encircling flange 19.

A hollow plunger 20 is slidably disposed within cylinder 14 and has a rubber sealing member 22 (FIG. 1A) secured at its right hand end, sealingly engaging the interior of the cylinder. The opposite end of the plunger 20 terminates in a flange 24 (FIG. 1).

The syringe is modified from conventional syringes. The forward end of plunger 20 has an opening 26 through which a valve stem 28 extends. The sealing member 22 has a small opening through which the stem 28 is forced, so as to provide a seal between the two.

Holder 10 is of open framework form and comprises a palm abutting hand piece 30, and a forwardly positioned syringe holder or crosshead 32, fixedly interconnected by an elongate pair of guide rails 36, 38. Guide rails 36, 38 are shown as having an interference fit with syringe holder 32, and are secured to the hand piece 30 by a pair of screws 40, 42 extending into recess openings 39, 41, respectively.

Syringe holder 32 is formed with a pair of channeled slots 34 which frictionably slidably receive flange 19 of syringe cylinder 14. In this manner, the position of syringe cylinder 14 is fixed relative to hand piece 30, guide rails 36, 38, and holder 32.

Guide rails 36, 38 extend through holes 35, 37 in a generally rectangular finger grip 44 such that finger grip 44 is slidable along the rails. Finger grip 44 includes two finger receiving portions 43, 45 for receiving two fingers. Finger grip 44 is formed with a pair of slots 46 which slidably and frictionally receive and detachably retain flange 24 of plunger 20. Accordingly, movement of finger grip 44 causes plunger 20 to be moved relative to syringe cylinder 14.

Finger grip 44, and correspondingly plunger 20, is biased toward a forward, discharge position by a pair of springs 48, 50 encircling lower rail 38 between hand piece 30 and finger grip 44. A slidable annular ring 52 encircles rail 38 and separates springs 48, 50.

Within cylinder 14 of syringe 12 is the valve stem 28 having a needle valve 54 at its forward end. Needle valve 54 seats at the forward end of syringe 14 on a valve seat 55 formed in surrounding relation to the discharge orifice 16. The opposite end of valve stem 28 terminates in a button-like knob 56.

Holder 10 includes a valve stem extension member 58 which slidably extends at its forward end portion through a bore 47 in finger grip 44. Such portion is formed with a blind socket 60 in one side thereof (see FIG. 2), the socket having a narrow channel 61 extending from the socket to the right hand end of the extension member 58. The knob 54 slidingly but frictionally fits laterally within the socket 60 and channel 61 at the time the syringe flanges are fitted into place.

Accordingly, the syringe 12 incorporating valve stem 28 is removable from holder 10. Also, because the interconnection of stem extension member 58 and stem 28, movement of valve stem actuator 58 causes movement of valve stem 28 and correspondingly seating and unseating of needle valve 54 at discharge opening 16 on syringe 12.

The rearward end of extension member 58 is formed with a hole which threadedly receives a screw 62. The head of screw 62 is slidably received in a bore 68 formed in hand piece 30. The hand piece 30 has a counterbore 70 coaxial with bore 68. A spring 64 encircles screw 62 and bears at its opposite ends against the end of extension 58, and a shoulder 59 formed by the counterbore. In this manner, extension 58 is biased in the forward direction, which biases needle valve 54 in its forward closed or seated position.

A trigger 66 in the form of an angle rod has one leg extending through extension 58, and has its other leg slidably received within a blind hole 72 formed in the hand grip 30.

Pulling on trigger 66 causes extension 58 to be pulled rearwardly disengaging needle valve 54 from its seat. Releasing of the pulling force on the trigger results in valve 54 being reseated due to the biasing force of spring 64.

Operation

The device is intended to primarily be used for aspirating fluid or cells from a body but could also be used for injecting a material into a body.

To aspirate fluid, a user would first insert a syringe with associated valve stem into the holder such that the flange of the syringe is held by syringe holder 32 and the flange of the plunger is held by finger grip 44, the knob of the valve stem being received in socket 60 of valve stem extension 58. A user would then grasp the holder, with hand grip 30 bearing against the palm of the user's hand and two of the user's adjacent fingers being received in associated slots 43, 45 in hand grip 44.

The needle is then impaled in a body at the desired location, whereafter the finger grip 44 is pulled rearwardly, causing plunger 20 to be retracted. Because of friction between sealing member 22 and valve stem 28, as well as due to the aspirating effect of the withdrawing plunger, valve stem extension 58, valve stem 28, and its valve 54 are urged rearward against the resistance of the biasing spring 64. This action causes the valve to unseat (FIG. 3) to allow fluid to flow into needle 18 and perhaps into the syringe barrel.

When the desired amount of fluid is withdrawn into the needle and syringe, the pulling force is released, whereupon the springs 48, 50 urge the grip 44 and thus the plunger to the right, as shown in the figures. However, such rightward movement is very slight, because almost immediately the spring 64 automatically causes the valve to seat (FIG. 4), trapping fluid and air in the right-hand end of the cylinder between the plunger and the seated valve. This trapped air/fluid automatically retains the plunger in its withdrawn condition, preserving the sample fluid within the needle and the plunger.

The user then removes the needle from the body and locates the needle end over a slide or other sample receiving means. Then, using one of both of the two fingers (used to pull finger grip 44 rearward), the user trips the trigger 66. This unseats the valve 54 (FIG. 3), enabling the biasing force resulting from springs 48, 50 to force finger grip 44 and the corresponding plunger 20, forwardly to eject the fluid from the needle.

When the desired amount of fluid has been discharged, the user releases the pulling force on trigger 66 causing the needle valve to reseat and preventing further fluid from escaping.

As is readily apparent from the above description, a user need only use one hand to effect the aspiration and subsequent discharge of fluid leaving the other hand free for other uses.

The head of screw 62 preferably is prevented by an internal flange (located to the right of the head) from accidental dislodgment from the bore 68.

FIGS. 5 and 6 show an improved needle which is ideal for use with the syringe actuator of the present invention and/or the syringe itself, but has other uses.

Referring to FIG. 5, the needle has a solid conical tip 101 but a hollow tubular shank 103 having a central passage 104. The shank is formed with two axially elongate opposed openings, labeled 105 and 107. As shown in FIG. 6, the openings are formed so that they flare inwardly from the outer surface of the shank to provide sharp, almost knife edges 111 at the exterior of the needle.

In use, while the sample is being taken, or thereafter, the needle is pushed in and out several times so that the knife edges can sever cellular material that might be drawn into the openings, to facilitate taking a sample which includes not only fluids, per se, but also cells.

Modified Form of Invention

The modified form of the invention is like the FIG. 1 form, except as described below. The modified form differs primarily in that it has a special latch operable when activated to hold the valve open until the latch is tripped.

FIG. 7 shows that the valve stem/trigger combination of FIG. 1 has been retained. The stem 58a has its upper end slidably received within a bore 241 in the hand piece or butt member 30a, and is urged by a spring 64a toward a seating direction.

The tripper 66a comprises one arm of a multiple arm 272 actuator 266. The tripper arm slidably extends through a lateral bore 267 in the stem 58a. Just beyond the stem, the arm connects to three other arms 268, 270 and 272, in X, Y, Z fashion (see FIG. 9). Arms 268 and 270 lie along one axis, while tripper 66a on another, while arm 272 extends along the third axis. Arm 272 comprises a latch support arm which projects into a bore 274 formed in the butt member 30a.

The arm 272 has a latch element in the form of a head 281. The bore 274 is of a size to accommodate free axial movement at the head, the head being carried by the stem 58a. However, the bore 274 is formed with a latch shelf 283 (FIGS. 10 and 11).

The actuator is capable of cocking movement because, it, in effect, is rockably mounted, in that tripper arm 66a functions as a shaft, which can turn relative to stem 58a on which it is mounted. This cocking movement facilitates shifting latching head 281 over onto the latch shelf 283.

In operation, the user has the option of using the modified device in the same manner in which the device of FIG. 1 operates; that is, leaving the latch 281/283 inactive, the user can withdraw the finger grip and thus the plunger 20, to unseat the needle valve. Now, the user can release the finger grip, whereupon spring 64a causes the needle valve to seat. Then, whenever the user decides to eject the fluid/cell specimen, the user can unseat the valve by actuating the trigger arm 66a.

Or if the user elects to do so, the user can first latch the needle valve open by activating the latch 281/283. Then the user withdraws the plunger 20. Whenever the desired specimen has been taken, the user flips arm 268 to unlatch or inactivate the latch 281/283 to release the valve to permit it to close. Then arm 68a can be tripped to open the valve to eject the specimen.

Having illustrated and described the principles of my invention with reference to a preferred embodiment, it should be apparent to those persons skilled in the art that such invention may be modified in arrangement and detail without departing from such principles. We claim as our invention all such modifications as come within the true spirit and scope of the following claims.

We claim:

1. A syringe-type medical device for holding a syringe of the type having a syringe cylinder which slidably receives a plunger, the device comprising:
    a frame;
    the frame including means for removably holding the syringe cylinder;
    a movable finger-engaging member slidable on the frame from an initial position to a retracted position, the movable finger-engaging member having means for removably holding the plunger;
    a movable valve stem mounted on the frame;
    a spring urging said valve stem in a predetermined direction for valve seating purposes; and
    finger engaging means for applying a retracting and unseating force to the valve stem.

2. The syringe-type medical device of claim 1 wherein the movable finger-engaging member is spring biased in the direction of the initial position.

3. The syringe-type medical device of claim 1 wherein the valve stem includes means for removably retaining a valve engaging stem which engages and disengages a valve element connected thereto.

4. The syringe-type medical device of claim 1 wherein the valve stem slidably extends through the finger-engaging member.

5. The syringe-type medical device of claim 1 wherein the means for removably holding the syringe body and the means for removably retaining the plunger each comprise a pair of slots which are adapted to slidably receive and retain flanges on the syringe body and plunger, respectively.

6. A syringe type medical device as described in claim 1 wherein there are latch means for latching said valve stem in an unseated position.

7. A syringe comprising
    a generally cylindrical body including a discharge opening and a plunger receiving opening, the plunger receiving opening being wider than the discharge opening, the discharge opening being adapted to retain a hypodermic needle;
    a plunger slidably received within the cylindrical body, the plunger including resilient sealing means at a forwardmost end for retaining fluid within the cylindrical body;
    a valve engaging stem including a valve element at one end thereof, the valve engaging stem and valve element extending slidably through the plunger and resilient sealing means and being in sealing relationship with respect to the plunger;
    the cylindrical body including a valve seat at its discharge opening, the seat being sized and configured to receive the valve element for sealing the discharge opening with respect to the cylindrical body; and the valve element being engaged and disengaged by sliding movement of the valve engaging stem with respect to the cylindrical body.

8. The syringe of claim 7 wherein the valve element comprises a needle valve.

9. In combination, a medical device for holding a syringe, and a syringe, the syringe comprising a generally cylindrical body including a discharge opening and a plunger receiving opening, the plunger receiving opening being wider than the discharge opening, the discharge opening being adapted to retain a hypodermic needle, a plunger slidably received within the cylindrical body, the plunger including resilient sealing means at a forwardmost end for retaining fluid within the cylindrical body, a valve engaging stem including a valve element at one end thereof, the valve engaging stem and valve element extending slidably through the plunger and resilient sealing means and being in sealing relationship with respect to the plunger, the cylindrical body including a valve seat at its discharge opening, the seat being sized and configured to receive the valve element for sealing the discharge opening with respect to the cylindrical body; and the medical device for holding the syringe comprising a frame which includes means for removably holding the syringe cylindrical body, a movable finger-engaging member slidable on the frame from an initial position to a retracted position with the movable finger-engaging member having means for removably holding the plunger, a movable valve stem mounted on the frame having means for removably retaining the valve engaging stem whereby movement of the valve stem engages and disengages the valve element relative to the valve seat of the syringe, a spring urging said valve stem in a predetermined direction for causing seating of the valve element in the valve seat, and finger engaging means for applying a retracting and unseating force to the valve stem.

10. The combination of claim 9, further comprising a hypodermic needle comprising a tubular shank terminating in a solid conical tip, at least one hole formed in the wall of the tubular shank adjacent the tip, said hole being defined in part by a sharp edge.

11. The combination of claim 10 wherein said sharp edge is provided by the convergence of the exterior wall of said shank and inwardly diverging walls of said hole.

* * * * *